(12) United States Patent
Belkin et al.

(10) Patent No.: US 8,529,907 B2
(45) Date of Patent: Sep. 10, 2013

(54) METHODS OF TREATING OPHTHALMIC DISORDERS

(75) Inventors: Michael Belkin, Givat Shmuel (IL); Aviv Shaish, Talmei Yehyel (IL); Dror Harats, Ramat Gan (IL); Ygal Rotenstreich, Kfar-Bilu (IL)

(73) Assignees: Nikken Sohonsha Corporation, Hashima, Gifu (JP); Tel Hashomer Medical Research Infrastructure and Services Ltd., Tel Hashomer (IL)

(*) Notice: Subject to any disclaimer, the term of this patent is extended or adjusted under 35 U.S.C. 154(b) by 0 days.

(21) Appl. No.: 12/989,817

(22) PCT Filed: Apr. 27, 2009

(86) PCT No.: PCT/IL2009/000448
§ 371 (c)(1),
(2), (4) Date: Oct. 27, 2010

(87) PCT Pub. No.: WO2009/133552
PCT Pub. Date: Nov. 5, 2009

(65) Prior Publication Data
US 2011/0045035 A1   Feb. 24, 2011

Related U.S. Application Data

(60) Provisional application No. 61/071,447, filed on Apr. 29, 2008, provisional application No. 61/202,336, filed on Feb. 19, 2009.

(51) Int. Cl.
*A61K 36/05*   (2006.01)
*A61P 27/02*   (2006.01)

(52) U.S. Cl.
USPC ............ 424/195.17; 424/408; 514/912

(58) Field of Classification Search
None
See application file for complete search history.

(56) References Cited

U.S. PATENT DOCUMENTS

| | | | |
|---|---|---|---|
| 5,948,823 | A * | 9/1999 | Ben-Amotz et al. |
| 7,264,813 | B2 * | 9/2007 | Shaish et al. |
| 2006/0185034 | A1 * | 8/2006 | Todd et al. |
| 2009/0169586 | A1 * | 7/2009 | Tracton |

FOREIGN PATENT DOCUMENTS

| | | |
|---|---|---|
| WO | 2006/086706 A2 | 8/2006 |
| WO | WO 2007109824 A1 * | 10/2007 |

OTHER PUBLICATIONS

Werman, MJ et al. Journal of Nutritional Biochemistry (2002); 13: 585-591. Bioavailability of the isomer mixture of phytoene and phytofluene-rich alga Dunaliella bardawil in rat plasma and tissues.*
Wernab, MJ et al. Journal of Nutritional Biochemistry (2002); 13: 585-591. Bioavailability of the isomer mixture of phytoene and phytofluene-rich alga Dunaliella bardawil in rat plasma and tissues.*
Friedman, D. S., et al., "Prevalence of Age-Related Macular Degeneration in the United States", Arch Ophthalmol., vol. 122, pp. 564-572, (2004).
Tracton, "Preparation of stabilized packaged dosage form e.g. for treating optical disorder, skin disorder, flu or cancer, involves storing oxidation-sensitive material in sealed container with oxygen scavenger and/or desiccant", DERWENT-Acc-No: 2007-805346; DERWENT-WEEK: 200945; five pages; (2006).
Noorwez, S. M., et al., "Retinoids Assist the Cellular Folding of the Autosomal Dominant Retinitis Pigmentosa Opsin Mutant P23H", The Journal of Biological Chemistry, vol. 279, No. 16, Issue of Apr. 16, pp. 16278-16284, (2004).
Van Hooser, J. P., et al., "Rapid restoration of visual pigment and function with oral retinoid in a mouse model of childhood blindness", PNAS, vol. 97, No. 15, pp. 8623-8628, (2000).
Van Hooser, J. P., et al., "Recovery of Visual Functions in a Mouse Model of Leber Congenital Amaurosis", The Journal of Biological Chemistry, vol. 277, No. 21, Issue of May 24, pp. 19173-19182, (2002).
Jimenez, C., et al., "Differential Reactivity of [beta]-Carotene Isomers from Dunaliella bardawil Toward Oxygen Radicals", Plant Physiol., vol. 101, No. 2, pp. 385-390 (1993). Abstract.
Orset, S., et al., "Spray-drying of the microalga Dunaliella salina: effects on beta-carotene content and isomer composition", J Agric Food Chem., vol. 47, No. 11, pp. 4782-4790, (1999). Abstract.

* cited by examiner

*Primary Examiner* — Michele C. Flood
(74) *Attorney, Agent, or Firm* — Vorys, Sater, Seymour and Pease LLP; Susanne M. Hopkins

(57) ABSTRACT

Provided is a method for improving day photopic vision and/or cone-derived visual field and visual function in a subject suffering from a retinal disease or trauma including administering to the subject a pharmaceutically effective amount of crude *Dunaliella* powder. Also provided is a method for improving night vision and/or rod derived visual field in a subject suffering from a retinal disease including administering to the subject a pharmaceutically effective amount of crude *Dunaliella* powder. A pharmaceutical composition for improving day vision and/or visual field in a subject suffering from a retinal disease including crude *Dunaliella* powder is also provided.

11 Claims, 7 Drawing Sheets

METHODS OF TREATING OPHTHALMIC DISORDERS

This is a National Phase Application filed under 35 U.S.C. 371 as a national stage of PCT/IL2009/000448, filed on Apr. 27, 2009, an application claiming the benefit under 35 USC 119(e) of U.S. Provisional Application No. 61/071,447, filed on Apr. 29, 2008, and an application claiming the benefit under 35 USC 119(e) of U.S. Provisional Application No. 61/202,336, filed on Feb. 19, 2009, the content of each of which is hereby incorporated by reference in its entirety.

FIELD OF THE INVENTION

This invention relates to methods of treating ophthalmic disorders, and to pharmaceutical compositions therefor.

BACKGROUND OF THE INVENTION

The human eye is capable of both day and night vision. Rod cells, or rods, are photoreceptor cells in the retina of the eye that can function in less intense light than can the other type of photoreceptor, cone cells. Being more light sensitive, rods are responsible for night vision. Named for their cylindrical shape, rods are concentrated in all parts of the retina except its center and thus provide peripheral vision. Cone cells, or cones, are photoreceptor cells in the center of the retina of the eye which function best in relatively bright light. The cone cells gradually become sparser towards the periphery of the retina.

Diseases of the eye may affect one type of vision or the other or both. In certain diseases, first night vision is affected, while day vision is affected as the disease progresses.

Retinitis pigmentosa (RP) comprises a group of relatively common inherited diseases characterized by progressive degeneration of the retina of the eye. The continually spreading destruction of the retina leads to increasingly severe visual loss. Vision gradually degenerates from the periphery [night vision, wide visual field] to the center [high definition day vision, colors]. Symptoms start with a decrease in dark adaptation leading to night blindness. There is a simultaneous reduction in the peripheral field of view up to tunnel vision. Central (day) vision is subsequently lost leading to total blindness. The rate of progression of RP varies according to the specific genetic defect. The visual impairment problem is much more prevalent than blindness.

Currently, no treatment is recognized to improve the vision of RP patients. Vitamin A palmitate (15,000 U/d) is prescribed to slow the progress of RP by about 2% per year. Current clinical trials are underway to attempt to slow degeneration, and include:

Ciliary Neurotrophic Factor eye Implant
Omega 3 amino acid (DHA)
Lutein (10 or 30 mg/day) capsules
Vitamin A
Vitamin E Over the last 15 years, researchers have pinpointed defects in dozens of genes causing different forms of RP. Surprisingly, in some cases, patients with the same genetic defect can show different severities of vision loss and rates of disease progression. This effect is most dramatic across the retina of some individuals where regions with normal vision can abut regions of no vision. Environmental factors have been near the top of the suspect list for this variation in severity. An environmental factor experienced by all, but to varying extents, is exposure to light bright lights have been previously speculated to accelerate certain forms of RP.

About 100 mutations in the rhodopsin gene have been shown to cause RP but understanding of the steps between mutant proteins and death of rod photoreceptors remains incomplete. Many of the patients with rhodopsin mutation are known to have better prognosis while other suffer from blindness since early childhood with rapid degeneration.

Another eye disease is Leber's congenital amaurosis (LCA). RP and LCA are not the same disease although a few of the genes are common.

A large majority of blindness and low vision in developed countries is due to Age Related Macular Degeneration (AMD), a disease which involves destruction of the photoreceptors. AMD affects more than 1.75 million individuals in the United States. Owing to the rapid aging of the US population, this number will increase to almost 3 million by 2020 (*Arch Ophthalmol.* 2004; 122:564).

Night blindness also occurs in non-degenerative eye diseases. Examples of such diseases include congenital night vision disorder, congenital stationary night blindness, fundus albipunctatus and vitamin A deprivation syndrome. Congenital stationary night blindness is an inherited eye disorder that principally affects the rod photoreceptors in the retina, impairing night vision. There may also be moderate to high myopia (short sightedness). Under good lighting conditions, there is usually no visual deficit. There are several different types of the disorder which are inherited in an autosomal dominant, autosomal recessive, or X-linked recessive manner. The X-linked type affects almost exclusively males and accounts for the predominance of males with congenital stationary night blindness.

WO 2007/109824 discloses a process for preparing a stable packaged dosage form comprising an oxidation-sensitive material such as carotenes and carotenoids in whole dried algae of the genus *Dunaliella*. The dosage form is described as being useful in the treatment of a plurality of diseases including optical disorders such as macular degeneration or cataracts.

J. Preston Van Hooser, Tomas S. Aleman, Yu-Guang He, Artur V. Cideciyan, Vladimir Kuksa, Steven J. Pittler, Edwin M. Stone, Samuel G. Jacobson, Krzysztof Palczewski (2000) *Rapid restoration of visual pigment and function with oral retinoid in a mouse model of childhood blindness*. PNAS, vol. 97 no. 15, 8623-8628, analyzed retinoid flow in Rpe65-deficient mice, a model of Leber congenital amaurosis, which have no rod photopigment and severely impaired rod physiology. They intervened by using oral 9-cis-retinal, attempting to bypass the biochemical block caused by the genetic abnormality. Within 48 h, there was formation of rod photopigment and dramatic improvement in rod physiology.

J. Preston Van Hooser, Yan Liang, Tadao Maeda, Vladimir Kuksa, Geeng-Fu Jang, Yu-Guang He, Fred Rieke, Henry K. W. Fong, Peter B. Detwiler, and Krzysztof Palczewski (2002) *Recovery of Visual Functions in a Mouse Model of Leber Congenital Amaurosis*. J. Biol. Chem., Vol. 277, Issue 21, 19173-19182, provide evidence that early intervention by 9-cis-retinal administration significantly attenuated retinal ester accumulation and supported rod retinal function for more than 6 months post-treatment. In single cell recordings rod light sensitivity was shown to be a function of the amount of regenerated isorhodopsin; high doses restored rod responses with normal sensitivity and kinetics.

Syed M. Noorwez, Ritu Malhotra, J. Hugh McDowell, Karen A. Smith, Mark P. Krebs|, and Shalesh Kaushal (2004) *Retinoids Assist the Cellular Folding of the Autosomal Dominant Retinitis Pigmentosa Opsin Mutant P23H*. J. Biol. Chem., Vol. 279, Issue 16, 16278-16284, demonstrate that the mutant opsin P23H, associated with autosomal dominant retinitis pigmentosa, is effectively rescued by 9- or 11-cis-retinal, the native chromophore. P23H rhodopsins containing 9- or 11-cis-retinal had blue-shifted absorption maxima and altered photo-bleaching properties compared with the corresponding wild-type proteins.

There is no description in the scientific literature of a treatment causing an improvement in day vision of an RP patient.

SUMMARY OF THE INVENTION

In a first aspect of the present invention, there is provided a method for improving day [photopic] vision and/or cone-derived visual field and visual functions in a subject suffering from a retinal disease or trauma comprising administering to the subject a pharmaceutically effective amount of crude *Dunaliella* powder.

In the present specification, the term day vision or photopic vision relates to vision in bright light generated by the central portion of the retina, as opposed to night vision which is generated by the peripheral portion of the retina. Day vision is predominantly mediated by the cone cells in the retina.

In the present specification, the term retinal disease or trauma may include all types of retinal dystrophies in which degeneration of the retina leads to deterioration in day vision. Acquired retinal degenerations such as Age-related Macular Degeneration may also be included in this term. In one embodiment, retinal diseases which have a night vision stage or component are also included, but in such cases the invention relates only to the day vision stage or component. In another embodiment, the retinal disease is a retinal degenerative disease.

The active ingredient in accordance with the invention is a substantially crude *Dunaliella* algae preparation, typically dried *Dunaliella* algae. The *Dunaliella* algae are preferably *Dunaliella bardawil*. Other species include *D. salina, D. viridis, D. peircei, D. parva, D. media, D. euchlora, D. minuta, D. tertiolecta, D. primolecta, D. acidophila, D. quartolecta* and *D. polymorpha*.

In a preferred embodiment, the substantially crude *Dunaliella* algae preparation contains β-carotene (BC) at an approximately 1:1 ratio of 9-cis to all-trans isomers of BC or greater than 1:1 ratio of 9-cis to all-trans isomers of BC.

The terms "treating" or "treatment" in the present specification should be understood as bringing about an improvement in the pathological symptoms of the disease, and in some cases curing the disease.

An "effective amount" should be understood as an amount or dose of the active ingredient which is sufficient to achieve the desired therapeutic effect, i.e. treatment of the indicated diseases. The effective amount depends on various factors including the severity of the disease, the administration regimen, e.g. whether the preparation is given once or several times over a period of time, the physical condition of the subject; etc. The artisan should have no difficulties, by minimal experiments, to determine the effective amount in each case.

The crude *Dunaliella* powder is preferably administered orally, for example in an encapsulated form. However, other forms of administration are contemplated such as *Dunaliella* powder formulated with pharmaceutically-acceptable excipients for topical, intravenous, intramuscular, intraperitoneal or subcutaneous administration.

Suggested medical conditions for treatment in accordance with the present teachings include the following:

Retinitis pigmentosa (RP), Leber congenital amaurosis (LCA), Age-related macular degeneration (AMD), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, Birdshot Retinochoroidopathy, Multiple Evanescent White-dot syndrome, Acute Zonal Occult Outer Retinopathy, Retinal vein occlusion, Retinal artery occlusion, Diabetic retinopathy, Retinal toxicity, Retinal injury, Retinal traumata and Retinal laser lesions, and Fundus Albipunctata.

As used herein, the term "age-related macular degeneration or dystrophy" or "AMD" refers to a debilitating disease, which include wet and dry forms of AMD. The dry form of AMD, which accounts for about 90 percent of all cases, is also known as atrophic, nonexudative, or drusenoid macular degeneration. With the dry form of AMD, drusen typically accumulate in the retinal pigment epithelium (RPE) tissue beneath/within the Bruch's membrane. Vision loss can then occur when drusen interfere with the function of photoreceptors in the macula. The dry form of AMD results in the gradual loss of vision over many years. The dry form of AMD can lead to the wet form of AMD. The wet form of AMD can progress rapidly and cause severe damage to central vision. The macular dystrophies include Stargardt Disease, also known as Stargardt Macular Dystrophy or Fundus Flavimaculatus, which is the most frequently encountered juvenile onset form of macular dystrophy, and Best dystrophy also known as vitelliform macular dystrophy, cone-rod dystrophy and others included in the list above.

A further embodiment of this aspect of the invention is a pharmaceutical composition for improving day vision and/or visual field in a subject suffering from a retinal degenerative disease comprising crude *Dunaliella* powder.

In a second aspect of the present invention, there is provided a method for improving night vision and/or rod derived visual field in a subject suffering from a retinal night vision disease comprising administering to the subject a pharmaceutically effective amount of crude *Dunaliella* powder. Patients with this disease have difficulty adapting to low light situations due to impaired photoreceptor transmission.

In the present specification, the term night vision relates to vision in dim light generated by the peripheral portion of the retina. Night vision is predominantly mediated by the rod cells in the retina.

In the present specification, the term retinal disease may include all types of retinal dystrophies which are stationary and which lead to deterioration in night vision. Examples of such diseases include congenital night vision disorder, congenital stationary night blindness, fundus albipunctatus and vitamin A deprivation syndrome. In one embodiment, retinal degenerative diseases which have a day vision stage or component are also included, but in such cases the invention relates only to the night vision stage or component. In another embodiment, the retinal disease is a retinal degenerative disease.

The active ingredient in accordance with the invention is a substantially crude *Dunaliella* algae preparation, typically dried *Dunaliella* algae. The *Dunaliella* algae are preferably *Dunaliella bardawil*. Other species include *D. salina, D. viridis, D. peircei, D. parva, D. media, D. euchlora, D. minuta, D. tertiolecta, D. primolecta, D. acidophila, D. quartolecta* and *D. polymorpha*.

In a preferred embodiment, the substantially crude *Dunaliella* algae preparation contains β-carotene (BC) at an approximately 1:1 ratio of 9-cis to all-trans isomers of BC or greater than 1:1 ratio of 9-cis to all-trans isomers of BC.

The meanings of the terms "treating", "treatment" and "effective amount" are as defined above.

A further embodiment of this aspect of the invention is a pharmaceutical composition for improving night vision and/or rod-derived visual field in a subject suffering from a retinal degenerative disease comprising crude *Dunaliella* powder.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
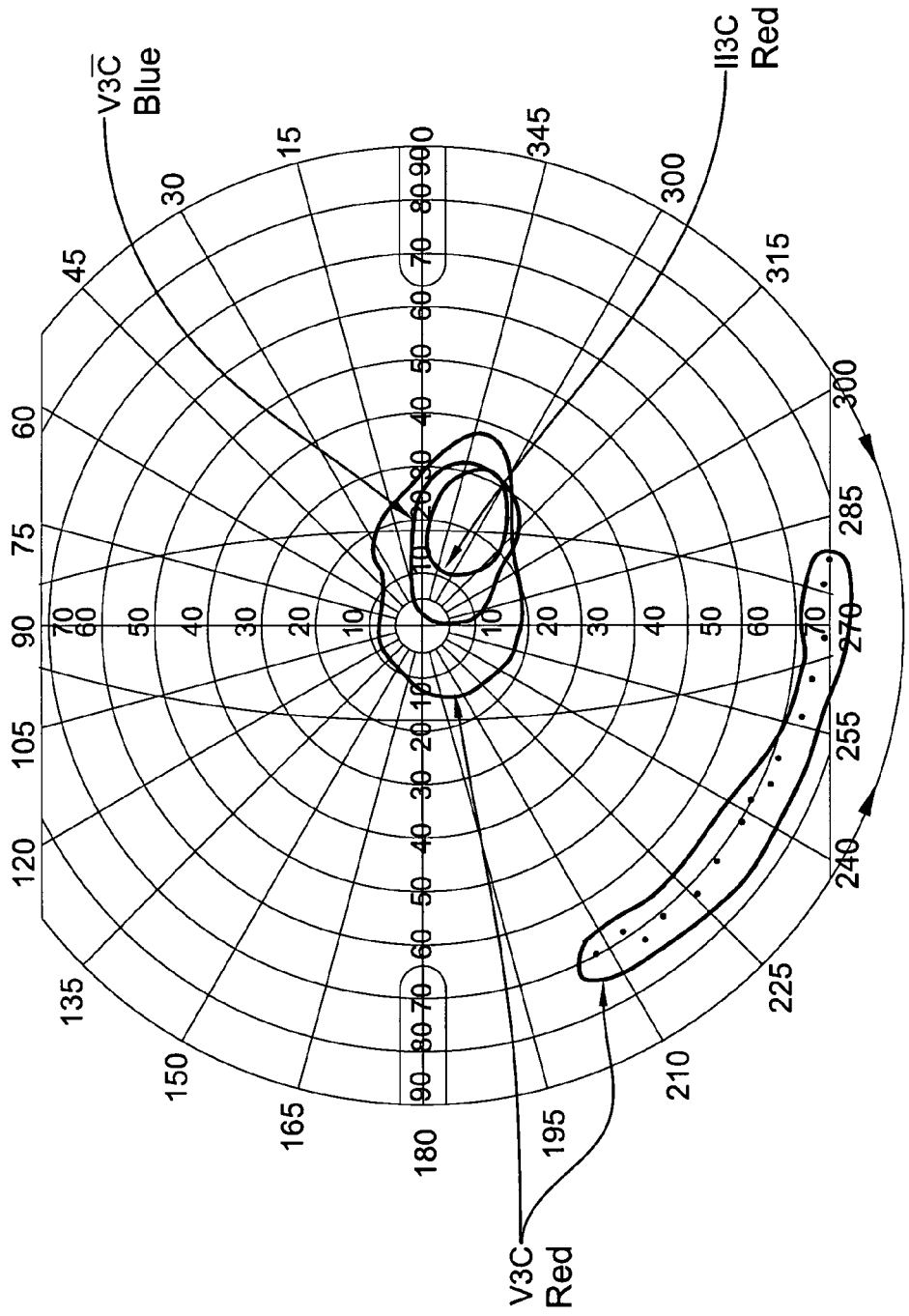
FIG. 1 is a dark-adapted chromatic visual field diagram of the left eye of an RP patient before treatment.
Figure 2:
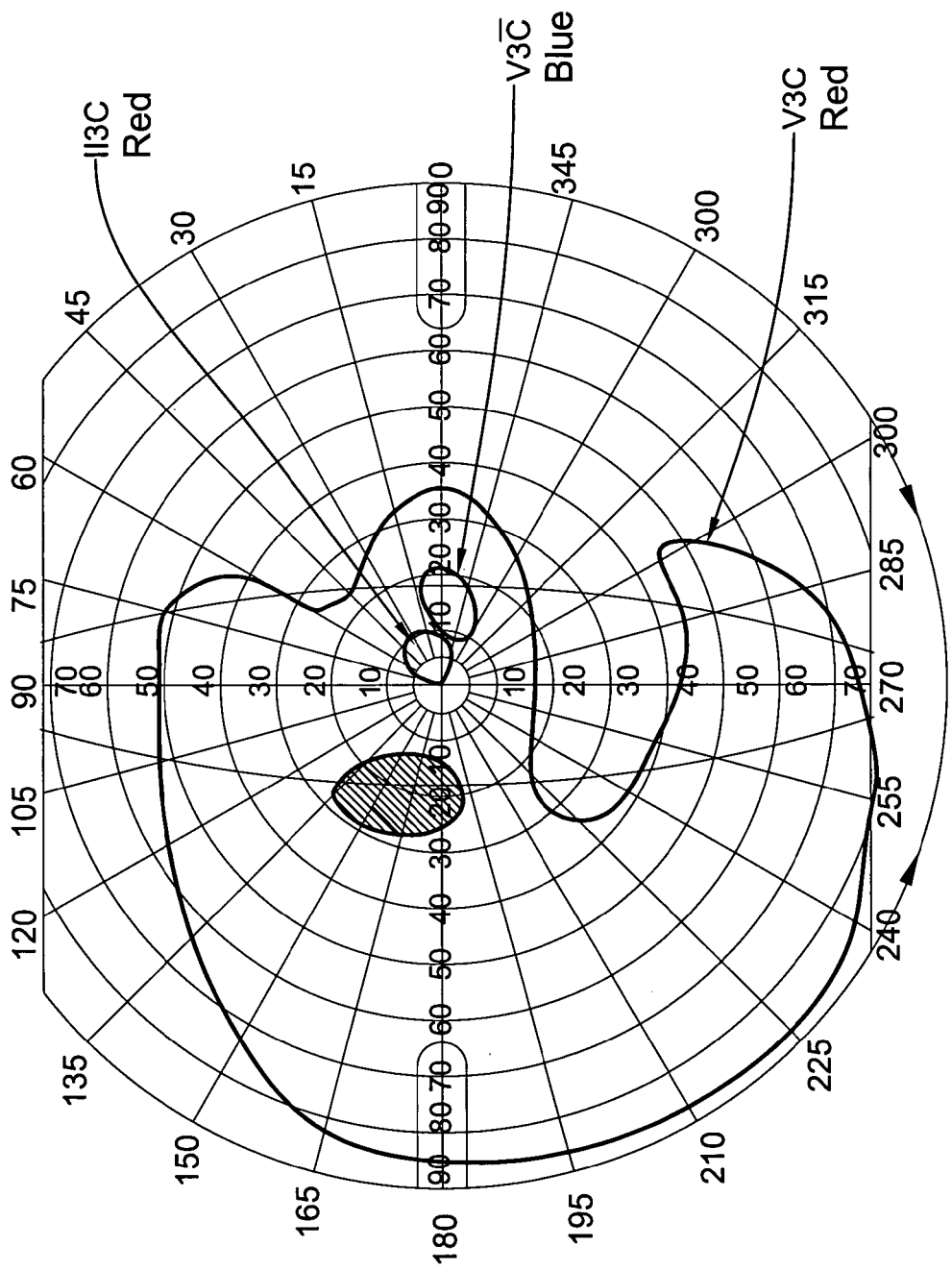
FIG. 2 is a dark-adapted chromatic visual field diagram of the left eye of an RP patient after 3 months of treatment.
Figure 3:
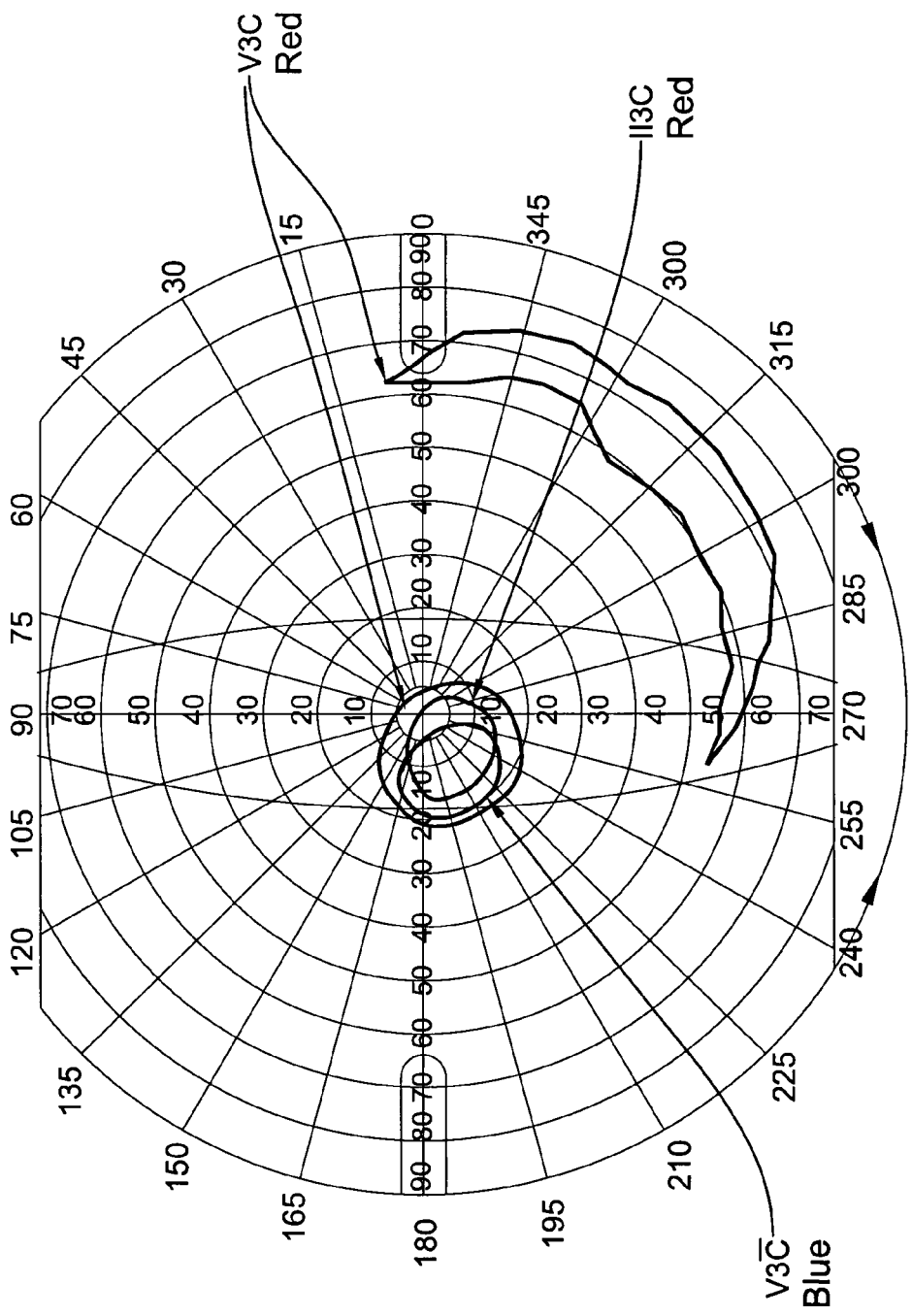
FIG. 3 is a dark-adapted chromatic visual field diagram of the right eye of an RP patient before treatment.
Figure 4:
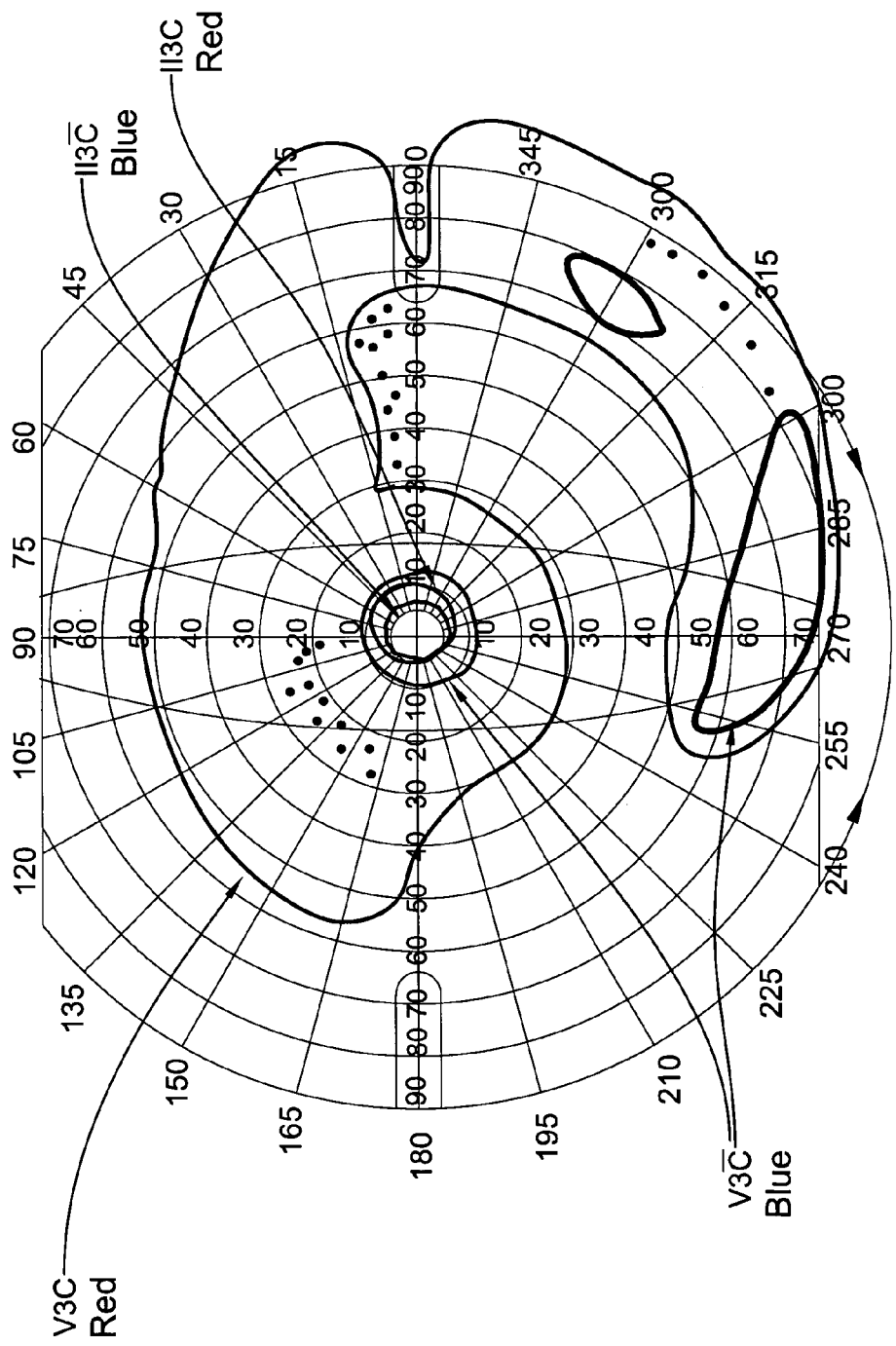
FIG. 4 is a dark-adapted chromatic visual field diagram of the right eye of an RP patient after 3 months treatment.

All of the human studies described below employed capsules containing *Dunaliella* powder prepared as follows.

*Dunaliella bardawil* (hereinafter "Db") was grown and cultivated in large body open salt water ponds of 50,000 m$^2$ to obtain algae comprising approximately 8% by weight of β-carotene (hereinafter "BC") at an approximately 1:1 ratio of 9-cis and all-trans isomers of BC, or greater than 1:1 ratio of 9-cis and all-trans isomers of BC. The algae were harvested by dislodging centrifuges into a concentrated paste. The paste was washed to remove the salt and sterilized, and then spray dried to yield Db powder comprising approximately 8% BC and less than 5% moisture. The powder was packaged in capsules of 250-300 mg algae containing 15-20 mg of BC each together with all of the natural components of the algae. The BC of the capsules retains the original ratio of isomers. The capsules are packaged in vacuum closed blisters which have a shelf life of up to three years.

EXAMPLE I

The Effect of Oral Administration of 9-Cis Rich Powder of the Alga *Dunaliella bardawil* on Day Vision Visual Functions in Patients with RP In a double-blind, placebo controlled, cross-over designed clinical trial, 20 patients (ages 50-75) with autosomal dominant retinitis pigmentosa (with RHO mutation) received 2 capsules twice a day for 12 weeks. Half of the patients received *Dunaliella baraweil* while the other half received placebo. The treatment period will be followed by a 12 week washout period and subsequently by a further 12 week period in which the patients who received *Dunaliella baraweil* will receive placebo, and vica versa. Four patients completed the first treatment period.

Results: out of 5 of the patients who completed the course of the treatment, two patients (#2 & #5) showed no improvement. On the other hand, the visual functions of the three other patients improved dramatically both objectively (ERG) and subjectively (visual fields and patients' report). These are unprecedented results for RP. It is assumed that these patients received the *Dunaliella* treatment.

One patient showed an improvement of 30% in photopic electroretinography (ERG) responses. Results for a second patient (#4) are presented in FIGS. 1-5. FIGS. 1-4 show the dark-adapted chromatic visual fields of the left and right eyes of the patient before and after the treatment. The subject is looking at the center and the observer shows him a small light stimulus in the periphery. The colored circles represent when the subject first observes the stimuli. Red stimulus is represented by a red circle and blue stimulus is represented by blue. The numbers II3C means size II (smaller compared to V), 3C represents the light intensity and the dash above C represents 100 times smaller light intensity.

| Relative Intensity | |
|---|---|
| 1 | 0.0315 |
| 2 | 0.100 |
| 3 | 0.315 |
| 4 | 1.00 |
| a | 0.40 |
| b | 0.50 |
| c | 0.63 |
| d | 0.90 |
| e | 1.00 |

| Object | |
|---|---|
| | mm$^2$ |
| O | 1/16 |
| I | 1/4 |
| II | 1 |
| III | 4 |
| IV | 18 |
| V | 64 |

Figure 5:
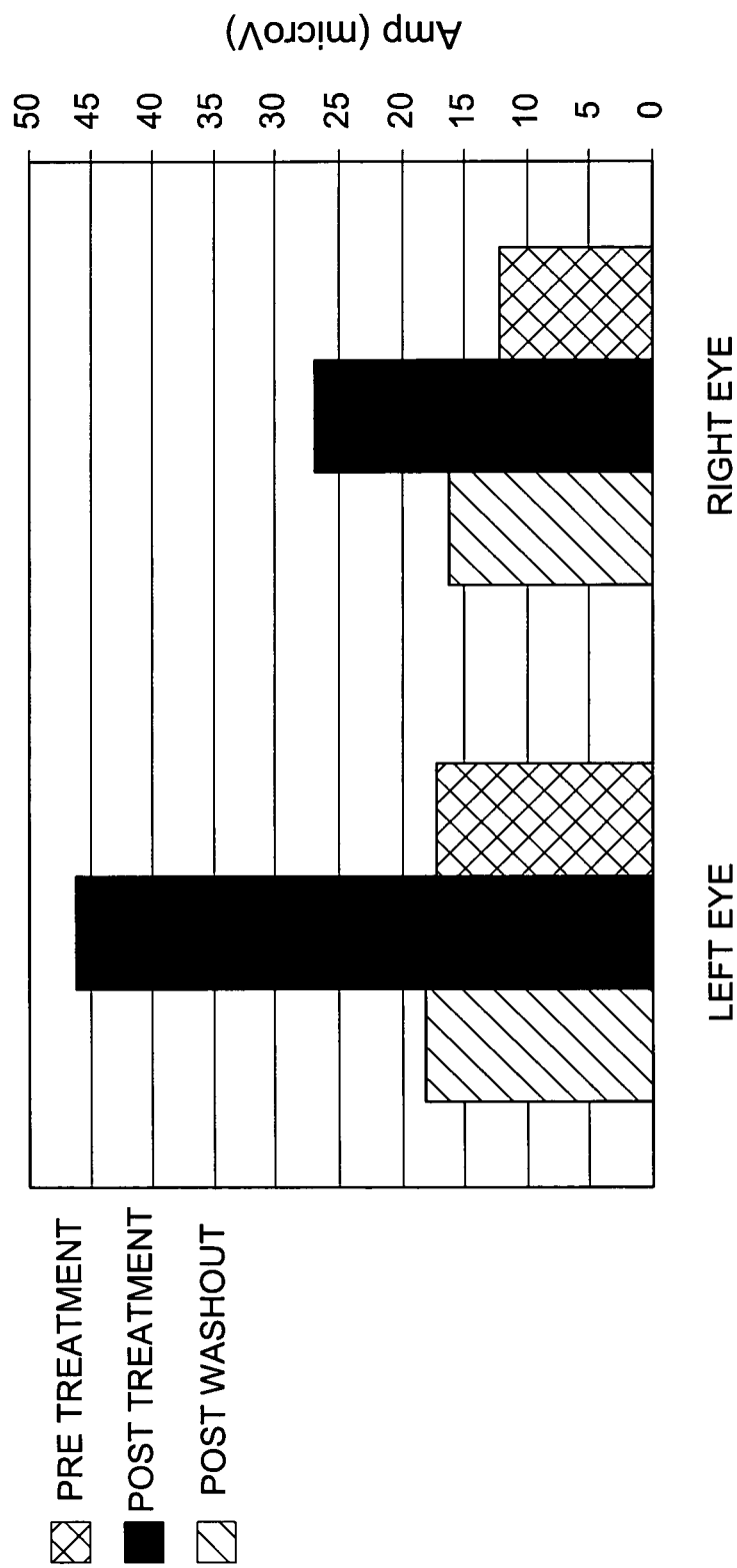
FIG. 5 is a bar graph showing photoreceptor ERG response levels pre-treatment, after treatment and after a washout period of 3 months in the left and right eyes of an RP patient.

Photoreceptor ERG results are presented in FIG. 5. It may be seen that both eyes showed marked improvement after treatment. The ERG returned to pretreatment levels 3 months after cessation of treatment. This indicates that maintenance treatment is required to maintain visual function.

EXAMPLE II

Further Results in the Day (Cone) Vision of Patients Enrolled in the Clinical Trial of Example I Additional patients subsequently completed the 3 month treatment period. The visual field and electrical function results for 5 patients are presented in Tables 1 and 2.

TABLE 1

Central (cone derived) visual field area

| | Right Eye | | Left Eye | |
|---|---|---|---|---|
| Patient | Pretreatment | Post treatment | Pretreatment | Post treatment |
| 1 | 9 | 19 | 9 | 14 |
| 2 | 184 | 185 | 189 | 183 |
| 3 | 90 | 131 | 96 | 141 |
| 4 | 159 | 159 | 145 | 137 |
| 5 | 164 | 165 | 177 | 185 |

TABLE 2

Cone electrical function (in µV)

| | Right Eye | | Left Eye | |
|---|---|---|---|---|
| Patient | Pretreatment | Post treatment | Pretreatment | Post treatment |
| 1 | 10 | 13 | 10 | 10 |
| 2 | 10 | 8 | 10 | 7 |
| 3 | 15 | 15 | 9 | 19 |
| 4 | 9 | 19 | 11 | 19 |
| 5 | 17 | 25 | 27 | 25 |

Figure 6A:
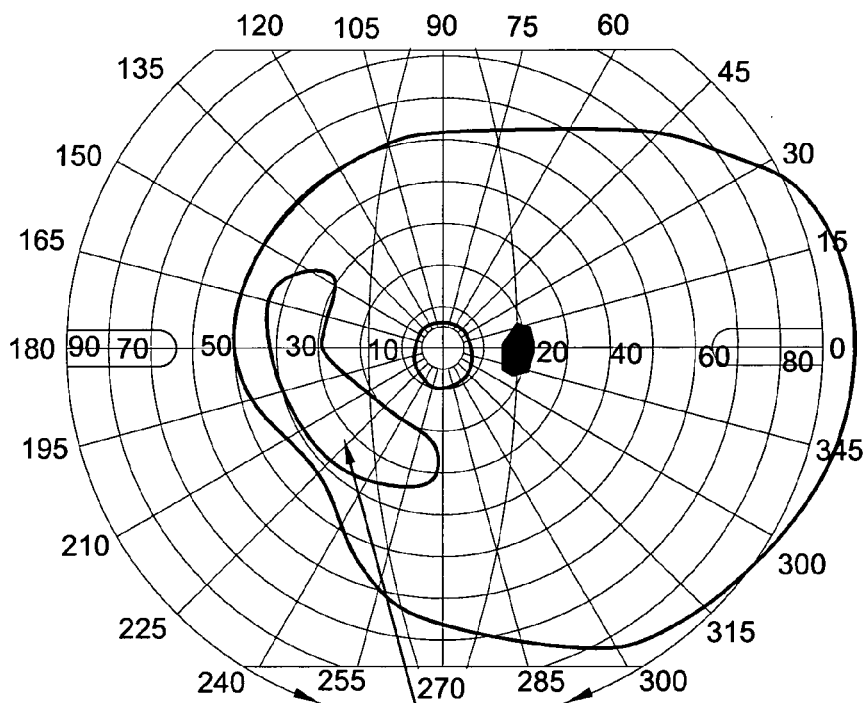
FIG. 6 is a dark-adapted chromatic visual field diagram of the right eye of patient #4 before (A) and after 3 months (B) of *Dunaliella* treatment showing the Scotoma (blind spot)
Figure 6B:
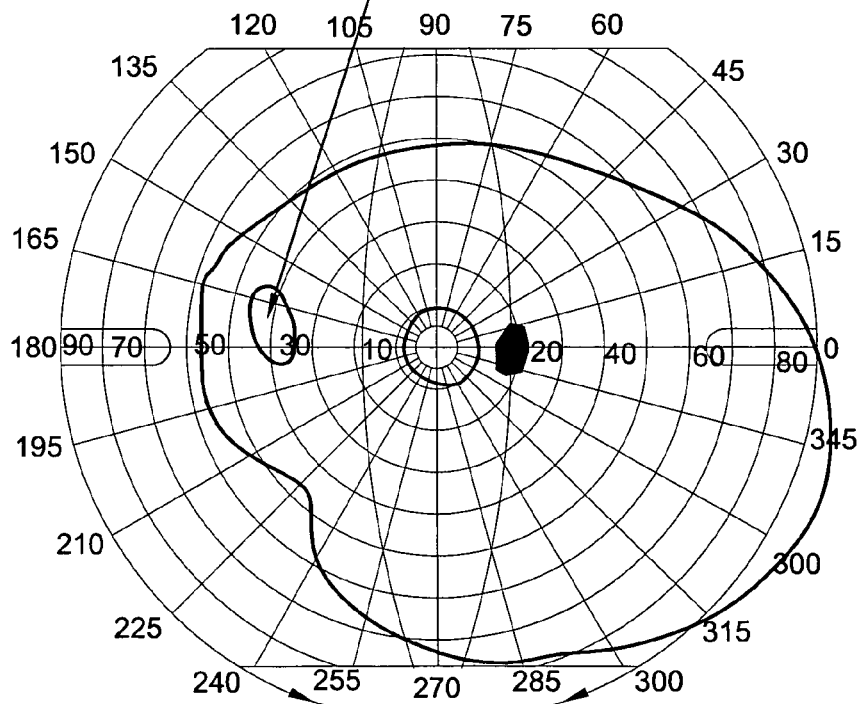

From the above results it may be seen that Patient #3 showed significant improvement in the visual field in both eyes and the ERG of one eye. Patients #4 showed no change in the cone derived area which was already within the normal limits prior to treatment. However, the blind spot in the right eye decreased significantly by a factor of 3.5 (FIG. 6). The cone electrical function showed significant improvement in patient #4 as well as in one of the eyes of patient #3. It is assumed that these patients received the *Dunaliella* treatment. There was no appreciable improvement in patients #2 &5.

EXAMPLE III

The Effect of Oral Administration of 9-Cis Rich Powder of the Alga *Dunaliella Bardawil* on Visual Functions in Patients with Dry Age-Related Macular Degeneration (AMD)

A clinical trial similar to the one described in Example I above will be carried out with patients with dry Age-related Macular Degeneration.

A preliminary study was carried out with a 74 years old woman suffering from a years-long deteriorating AMD in both eyes. The woman has not been able to read for the last few years. Within a week of receiving the *Dunaliella* treatment at a dose of 4 capsules daily, she returned to normal reading in both eyes, although there was no improvement in the morphological appearance in ophthalmoscopy and OCT.

EXAMPLE IV

The Effect of Oral Administration of 9-Cis Rich Powder of the Alga *Dunaliella Bardawil* on Visual Functions in Patients with Congenital Stationary Night Blindness Subjects
Normal subjects: Five subjects without any pathology under ophthalmic examination, aged 58.6±5.6 years old, were treated daily for ninety days with four capsules of *Dunaliella* Bardawil as described above. The subjects were tested before treatment and after ninety days of treatment for visual acuity, biomicroscopic examination intraocular pressure and electroretinogram (ERG) tests. Normal subjects and patients performed visual fields central 24-2 threshold test before and after treatment in both eyes (the amblyopic eye was excluded).

Patients: Five patients, age 32±11 years old, with clinically and genetically diagnosed Congenital stationary night blindness (CSNB) were treated daily with four capsules of *Dunaliella bardawil* for 90 days.

The subjects were tested bilaterally before and after treatment by ERG (LKC Technologies, Inc., Gaithersburg, Md.) using an ISCEV compliant protocol. The scotopic responses were recorded for dim single flash stimulus (0.023 cd–s/m2) and bright single flash stimulus (2.44 cd–s/m2). Light adaptation for 10 minutes of white background light (0.023 cd-s/m2) followed by white single flash stimulus (2.44 cd–s/m2) and white 2.44 cd–s/m2 30 Hz flicker. The patients were dark adapted for an additional 90 minutes after recording the scotopic ERG 30 minutes (total of 120 minutes dark adaptation) and were then light adapted. The amplitudes latencies of the wave form were measured and the percentages of change were calculated by subtraction of baseline ERG responses from post treatment responses and divided by the baseline responses for each eye.

Results

Prior to the treatment, the best-corrected visual acuity for all normal subjects and patients were 20/20 in both eyes except for one patient who had amblyopic eye with visual acuity of 20/200. The visual acuity did not change post treatment.

The averaged mean deviation before and after treatment did not show any statistical significant improvement for the normal subject group (T-test, p=0.291). Prior to treatment, the patients' averaged visual field mean deviation was −5.16±2.25. After treatment, the mean deviation improved significantly to −3.42±3.12 (T-test, p=0.019).

Figure 7:
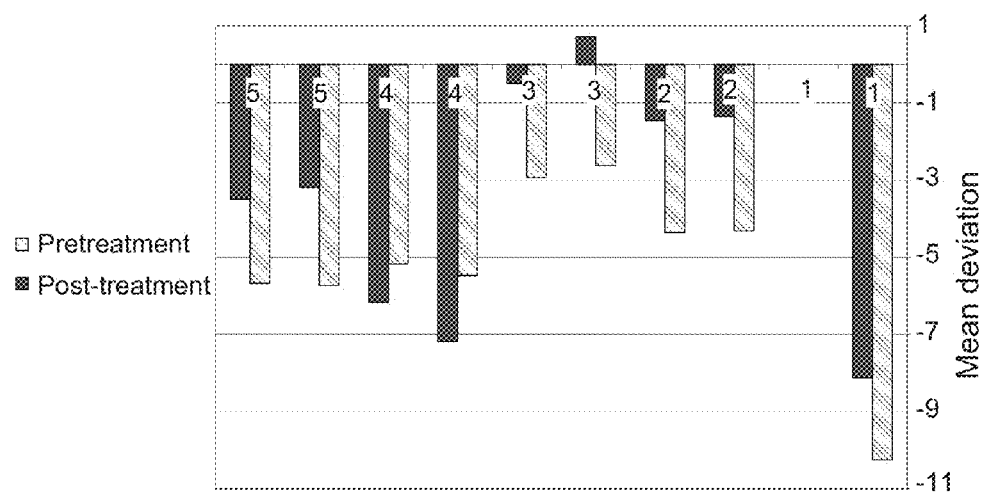
FIG. 7 is a bar graph showing the visual field mean deviation before and after treatment of normal subjects and patients.

The results are summarized in FIG. 7.

Electroretinogram (ERG)

Normal subjects: The ERG percentage of change responses of the normal subjects are summarized in Table 3. The average isolated rod response amplitude pre-treatment was 199±57 μV and post-treatment was 184±49 μV (p=0.340, T-test). The maximal scotopic a-wave and b-wave amplitude responses did not show any difference from baseline. The average a-wave pre-treatment was 186±61 μV and post-treatment was 181±28 μV (p=0.307, T-test). The average b-wave amplitude pre-treatment was 361±61 μV and post-treatment was 370±79 μV (p=0.615, T-test). The ERG responses in photopic conditions did not show any significant change from baseline. The average a-wave amplitude pre-treatment was 28±4 μV and post-treatment was 25±5 μV (p=0.451, T-test). The average b-wave amplitude pre-treatment was 106±24 μV and post-treatment was 108±26 μV (p=0.797, T-test). The 30 Hz flicker responses did not show significant differences from baseline with pre-treatment average amplitude of 73±12 μV and post-treatment average amplitude of 86±16 μV (p=0.099, T-test). However, one subject showed a clinical significant improvement of 90% in the 30 Hz response in both eyes. This improvement could not be statically evaluated in this small group of subjects.

TABLE 3

ERG percentage of change

| | Conditions | Averaged percentage of change from baseline |
|---|---|---|
| Scotopic | Isolated rod response (b-wave amplitude) | 3 ± 21% |
| | Maximal a-wave amplitude | −3 ± 8% |
| | Maximal b-wave amplitude | 2 ± 14% |
| Photopic | a-wave amplitude | 3 ± 23% |
| | b-wave amplitude | 4 ± 25% |
| | 30 Hz Flicker | 22 ± 37% |

Patients: The responses for the CSNB patients are summarized in Table 4. The maximal scotopic ERG responses for 30 minutes dark adaptation were not changed significantly from baseline (the a- and b-waves maximal rod responses were 15%±55% and 42%±109% respectively). However, the 120 minutes dark adaptation maximal ERG b-wave responses was doubled, the a- and b-waves maximal rod responses increased by 17%±52% and 68%±63% respectively. The average b-wave maximal response amplitude pre-treatment was 194±56 μV and post-treatment was 300±52 μV (p<0.001, T-test). After 120 minutes of dark adaptation the average isolated rod response b-wave amplitude improved from 86±40 μV at baseline to 184±105 μV after treatment (p<0.001, T-test). All patients demonstrated a clinically significant improvement in the b-wave maximal and Isolated rod responses amplitude which was found to be similar in both eyes of each patient. The photopic single flash a- and b-wave response and 30 Hz flicker response (Table 4) did not show significant differences (0.11-0.571).

TABLE 4

ERG responses

| | Conditions | Averaged percentage of change from baseline |
|---|---|---|
| Scotopic 30 Minutes dark adaptation | Isolated rod response (b-wave amplitude) | None measurable |
| | Maximal a-wave amplitude | 15 ± 55% |
| | Maximal b-wave amplitude | 42 ± 109% |
| Scotopic 120 Minutes dark adaptation | Isolated rod response (b-wave amplitude) | 112 ± 61% |
| | Maximal a-wave amplitude | 17 ± 52% |
| | Maximal b-wave amplitude | 68 ± 63% |
| Photopic | a-wave amplitude | 18 ± 59% |
| | b-wave amplitude | 29 ± 63% |
| | 30 Hz Flicker | −11 ± 33% |

Figure 8:
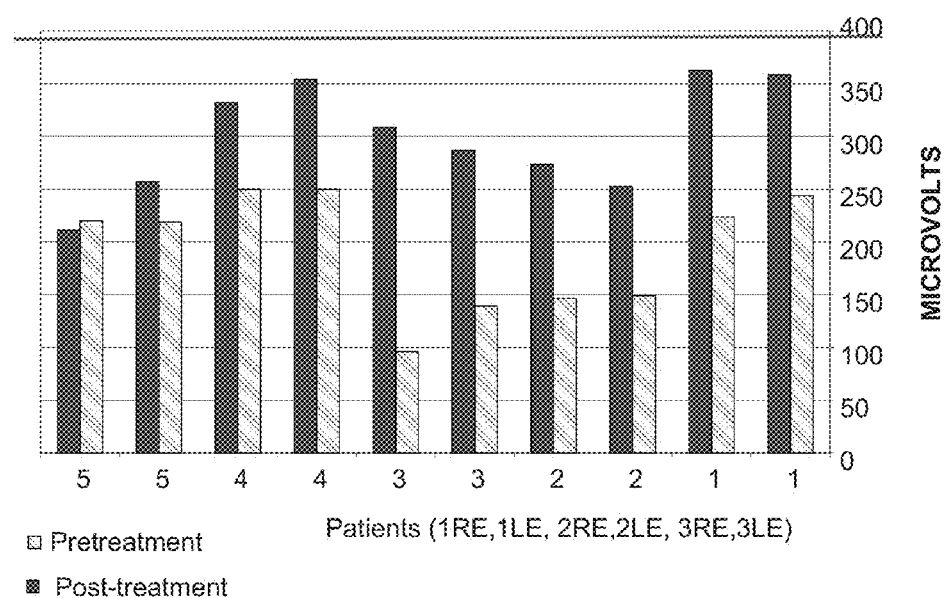
FIG. 8 is a bar graph showing the b-wave amplitude maximal responses before and after treatment of normal subjects and patients.

The results are summarized in FIG. 8.

Conclusions: Oral treatment with the algae *Dunaliella bardawil* significantly improved dark adaptation function in a number of congenital stationary night blindness patients.

Example V

Results in the Night Vision of Patients Enrolled in the Clinical Trial of Example I The night and peripheral vision field and electrical function results for the patients of Example II are presented in Tables 5 and 6.

TABLE 5

Visual field areas

| Patient | Right Eye Pretreatment | Right Eye Post treatment | Left Eye Pretreatment | Left Eye Post treatment |
|---|---|---|---|---|
| 1 | 7 | 7 | 9 | 7 |
| 2 | 97 | 143 | 102 | 123 |
| 3 | 61 | 64 | 61 | 68 |
| 4 | 18 | 130 | 22 | 127 |
| 5 | 137 | 165 | 113 | 139 |

TABLE 6

Rod electrical function (in μV)

| Patient | Right Eye Pretreatment | Right Eye Post treatment | Left Eye Pretreatment | Left Eye Post treatment |
|---|---|---|---|---|
| 1 | 11 | 11 | 11 | 11 |
| 2 | 20 | 21 | 25 | 25 |
| 3 | 23 | 30 | 21 | 26 |
| 4 | 10 | 48 | 16 | 106 |
| 5 | 15 | 15 | 21 | 36 |

The results show a significant improvement of the rod derived visual field area in both eyes of patient #4 and to a lesser extent in patients #2 & #5. The rod electrical function significantly improved in both eyes in patient #4 and to a lesser extent in the left eye of patient #5. It is assumed that these patients received the *Dunaliella* treatment.

The invention claimed is:

1. A method for improving day vision and/or cone-derived visual field and visual function in a subject suffering from a retinal disease comprising
administering to a subject in need thereof a pharmaceutically effective amount of a capsule dosage form comprising crude Dunaliella powder that is filled in a capsule under normal atmosphere to produce the capsule dosage form, the crude Dunaliella powder comprising β-carotene at an approximately 1:1 ratio of 9-cis and all-trans β-carotene isomers, or a greater than 1:1 ratio of 9-cis and all-trans β-carotene isomers.

2. The method of claim 1, wherein the retinal disease is selected from the group consisting of retinitis pigmentosa (RP); Leber congenital amaurosis (LCA), recessive RP; Dominant retinitis pigmentosa; X-linked retinitis pigmentosa; Incomplete X-linked retinitis pigmentosa, dominant; Dominant Leber congenital amaurosis; Recessive ataxia, posterior column with retinitis pigmentosa; Recessive retinitis pigmentosa with para-arteriolar preservation of the retinal pigment epithelial (RPE); Retinitis pigmentosa RP12; Usher syndrome; Dominant retinitis pigmentosa with sensorineural deafness; Recessive retinitis punctata albescens; Recessive Alstrom syndrome; Recessive Bardet-Biedl syndrome; Dominant spinocerebellar ataxia with macular dystrophy or retinal degeneration; Recessive abetalipoproteinemia; Recessive retinitis pigmentosa with macular degeneration; Recessive Refsum disease, adult form; Recessive Refsum disease, infantile form; Recessive enhanced S-cone syndrome; Retinitis pigmentosa with mental retardation; Retinitis pigmentosa with myopathy; Recessive Newfoundland rod- cone dystrophy; Retinitis pigmentosa sine pigmento; Sector retinitis pigmentosa; Regional retinitis pigmentosa; Senior-Loken syndrome; Joubert syndrome; Stargardt disease, juvenile; Stargardt disease, late onset; Dominant macular dystrophy, Stargardt type; Dominant Stargardt-like macular dystrophy; Recessive macular dystrophy; Recessive fundus flavimaculatus; Recessive cone-rod dystrophy; X-linked progressive cone-rod dystrophy; Dominant cone-rod dystrophy; Cone-rod dystrophy; de Grouchy syndrome; Dominant cone dystrophy; X-linked cone dystrophy; Recessive cone dystrophy; Recessive cone dystrophy with supernormal rod electroretinogram; X-linked atrophic macular dystrophy; X-linked retinoschisis; Dominant macular dystrophy; Dominant radial, macular drusen; Dominant macular dystrophy, bull's-eye; Dominant macular dystrophy, butterfly- shaped; Dominant adult vitelliform macular dystrophy; Dominant macular dystrophy, North Carolina type; Dominant retinal-cone dystrophy 1; Dominant macular dystrophy, cystoid; Dominant macular dystrophy, atypical vitelliform; Foveomacular atrophy; Dominant macular dystrophy, Best type; Dominant, progressive North Carolina macular dystrophy; Recessive macular dystrophy, juvenile with hypotrichosis; Recessive foveal hypoplasia and anterior segment dysgenesis; Recessive delayed cone adaptation; Macular dystrophy in blue cone monochromacy; Macular pattern dystrophy with type II diabetes and deafness; Flecked Retina of Kandori; Pattern Dystrophy; Dominant Stickler syndrome; Dominant Marshall syndrome; Dominant vitreoretinal degeneration; Dominant familial exudative vitreoretinopathy; Dominant vitreoretinochoroidopathy; Dominant neovascular inflammatory vitreoretinopathy; Goldmann-Favre syndrome; Recessive achromatopsia; Dominant tritanopia; Recessive rod monochromacy; Congenital red-green deficiency; Deuteranopia; Protanopia; Deuteranomaly; Protanomaly; Recessive Oguchi disease; Dominant macular dystrophy, late onset; Recessive gyrate atrophy; Dominant atrophia areata; Dominant central areolar choroidal dystrophy; X-linked choroideremia; Peripapillary choroidal atrophy; Dominant progressive bifocal chorioretinal atrophy; Progressive bifocal Chorioretinal atrophy; Dominant Doyne honeycomb retinal degeneration or Malattia Leventinese syndrome; Amelogenesis imperfecta; Recessive Bietti crystalline corneoretinal dystrophy; Dominant hereditary vascular retinopathy with Raynaud phenomenon and migraine; Dominant Wagner disease and erosive vitreoretinopathy; Recessive microphthalmos and retinal disease syndrome; Recessive nanophthalmos; Recessive retardation, spasticity and retinal degeneration; Recessive Bothnia dystrophy; Recessive pseudoxanthoma elasticum; Dominant pseudoxanthoma elasticum; Recessive Batten or Juvenile neuronal ceroid-lipofuscinosis; Dominant Alagille syndrome; McKusick-Kaufman syndrome; hypoprebetalipoproteinemia, acanthocytosis, palladial degeneration; Recessive Hallervorden-Spatz syndrome; Dominant Sorsby's fundus dystrophy; Oregon eye disease; Kearns-Sayre syndrome; Retinitis pigmentosa with developmental and neurological abnormalities; Bassen-Kornzweig Syndrome; Hurler disease; Sanfilippo disease; Scheie disease; Melanoma associated retinopathy; Sheen retinal dystrophy; Duchenne macular dystrophy; Becker macular dystrophy; Birdshot Retinochoroidopathy; Multiple Evanescent White-dot syndrome; Acute Zonal Occult Outer Retinopathy; Retinal vein occlusion; Retinal artery occlusion; Diabetic retinopathy; and Fundus Albipunctatus.

3. The method of claim 1, wherein the crude *Dunaliella* powder is administered orally.

4. The method of claim 1, wherein the *Dunaliella* is selected from the group consisting of *Dunaliella bardawil, D. salina, D. viridis, D. peircei, D. parva, D. media, D. euchlora, D. minuta, D. tertiolecta, D. primolecta, D. acidophila, D. quartolecta* and *D. polymorpha*.

5. The method of claim 1, wherein the retinal disease is age-related macular degeneration (AMD).

6. The method according to claim 1, wherein the capsule dosage form comprises crude *Dunaliella* powder present in an amount of from 250 to 300 milligrams (mg).

7. The method according to claim 6, wherein the crude *Dunaliella* powder comprises 8% β-carotene.

8. The method according to claim 1, wherein the crude *Dunaliella* powder comprises moisture.

9. The method according to claim 6, wherein the crude *Dunaliella* powder comprises 15-20 mg of β-carotene.

10. The method according to claim 6, wherein the crude *Dunaliella* powder comprises all natural components of the algae.

11. A method for improving day vision and/or cone-derived visual field and visual function in a subject suffering from Retinitis pigmentosa, comprising:
  administering to a subject in need thereof a pharmaceutically effective amount of a capsule dosage form comprising crude *Dunaliella* powder encapsulated under normal atmosphere, the crude *Dunaliella* powder comprising β-carotene at an approximately 1:1 ratio of 9-cis and all-trans β-carotene isomers, or a greater than 1:1 ratio of 9-cis and all-trans β-carotene isomers.

* * * * *